United States Patent [19]

Mendel

[11] 3,996,280

[45] Dec. 7, 1976

[54] POLYFLUOROALKOXY-SUBSTITUTED AROMATIC CARBOXYLIC AMIDES AND HYDROZIDES

[75] Inventor: Arthur Mendel, Vadnais Heights, Minn.

[73] Assignee: Riker Laboratories, Inc., Northridge, Calif.

[22] Filed: Sept. 19, 1975

[21] Appl. No.: 614,905

Related U.S. Application Data

[62] Division of Ser. No. 349,237, April 9, 1973, Pat. No. 3,923,885, which is a division of Ser. No. 57,350, July 22, 1970, Pat. No. 3,766,247.

[52] U.S. Cl. .................... 260/559 R; 260/448 AD; 260/473 R; 260/520 R; 260/521 H; 260/521 B; 260/544 D; 260/559 H
[51] Int. Cl.² ..................................... C07C 103/26
[58] Field of Search .................... 260/559 R, 559 H

[56] References Cited

UNITED STATES PATENTS

| 3,766,247 | 10/1973 | Mendel | 260/559 H X |
| 3,840,598 | 10/1974 | Lesher | 260/559 R |

OTHER PUBLICATIONS

Scherer et al., CA 62:7687f (1965).

*Primary Examiner*—Allen B. Curtis
*Assistant Examiner*—Thomas A. Waltz
*Attorney, Agent, or Firm*—Alexander, Sell, Steldt & DeLaHunt

[57] ABSTRACT

Acyl halides, esters, amides, hydrazides and salts as well as the acid form derived from aromatic acids substituted by polyfluoroalkoxy groups. These compounds are valuable as synthetic intermediates in the preparation of physiologically active compounds.

9 Claims, No Drawings

POLYFLUOROALKOXY-SUBSTITUTED AROMATIC CARBOXYLIC AMIDES AND HYDROZIDES

This is a division of application Ser. No. 349,237 filed Apr. 9, 1973 (now U.S. Pat. No. 3,923,885). Application Ser. No. 349,237 is itself a division of application Ser. No. 57,350 filed July 22, 1970 (now U.S. Pat. No. 3,766,247).

DETAILED DESCRIPTION

This invention relates to polyfluoroalkoxysubstituted aromatic carboxylic acids and amides, esters, acyl halides, hydrazides and salts derived therefrom. These compounds are useful as synthetic intermediates in the preparation of physiologically active compounds, such as local anesthetics and antiarrhythmics.

A preferred class of compounds of the invention are those having the formula:

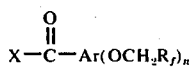
    I wherein X is amino (—NH$_2$), 2-haloethylamino, hydrazino (—NHNH$_2$), alkoxy (-OR wherein R is alkyl or CH$_2$R$_f$), halogen (selected from fluorine, chlorine and bromine), hydroxy or OM (wherein M is a metal ion), Ar is an aromatic carbocyclic system of 6 to 10 carbon atoms, each R$_f$ is a fluorocarbon group containing from one to three carbon atoms and $n$ is one to four. The complete fluorocarbon group (R$_f$) can be a fully or partially fluorinated alkyl group having a straight or branched structure. There can be no more than one hydrogen atom on any carbon atom and two carbon atoms in the R$_f$ group can be linked together by an oxygen atom. Thus, in addition to the optional oxygen atom, R$_f$ can contain only carbon, fluorine and hydrogen. A preferred class of the compounds of the invention is made up of those compounds in which R$_f$ is C$_m$F$_{2m}$Y, wherein $m$ is 1–3 and Y is hydrogen or fluorine.

A particularly preferred subclass of the compounds are those in which Ar is a naphthalene nucleus and $n$ is one. These compounds are particularly useful for the preparation of local anesthetics having activity of long duration. When X is 2-haloethylamino the halogen is chlorine or bromine.

A second preferred subclass consists of compounds in which Ar is a benzene nucleus and $n$ is one or two. These compounds are particularly useful for the preparation of antiarrhythmics of high potency.

Generally, compounds of the invention wherein R$_f$ is CF$_3$ are most preferred.

The metal ions (M) in the salts of the invention are preferably alkali metals (such as sodium and potassium), alkaline earths (such as magnesium and calcium), aluminum and the like.

Compounds of the invention wherein X is amino, —OR, halogen, hydrazino, hydroxy or OM are readily interconverted to one another by well-known synthetic procedures.

The compounds of Formula I, wherein X is OR, can be produced by reacting a compound of Formula II with an alkylating ester, for example a fluoroalkyl trifluoromethanesulfonate of Formula III, as shown in the following equation:

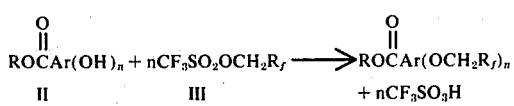

wherein R is alkyl and Ar, R$_f$ and $n$ are as defined hereinabove.

This reaction is carried out in the presence of sodium carbonate or potassium bicarbonate in an inert solvent such as acetone. Alternatively compounds of Formula II wherein R is hydrogen may be reacted with $n + 1$ moles of compounds of Formula III to give compounds of Formula I wherein X is —OCH$_2$R$_f$.

The esters of Formula I may be hydrolyzed to the free acid (Formula I, X = OH).

Compounds of Formula I wherein X is halogen are conveniently prepared by refluxing the corresponding esters of Formula I (compounds wherein X is OR) with an excess of thionyl chloride in the presence of a small amount of dimethylformamide. Other conventional methods for the synthesis of acyl halides may also be useful.

Compounds of Formula I wherein X is amino (that is, amides) are conveniently prepared from compounds of Formula I wherein X is halogen by reaction with ammonia, from esters of Formula I by reaction with concentrated ammonium hydroxide and other well-known synthetic methods.

Compounds of Formula I where X is hydrazino are most commonly prepared by treating the ester or acyl halide of Formula I with 40 per cent aqueous hydrazine hydrate solution.

Compounds of Formula I wherein X is —OH (that is, acids) are prepared by hydrolysis of compounds of Formula I wherein X is halogen, amino, hydrazino or —OR, or by acidification of compounds of Formula I wherein X is —OM.

Compounds of Formula I wherein X is —OM are most conveniently prepared by reaction of acids of Formula I with metal hydroxides or alkoxides, but may also be prepared by hydrolysis of esters, amides, hydrazides and acyl halides of Formula I with metal hydroxides and alkoxides under conditions which modify the rates of these sometimes strongly exothermic hydrolyses.

Compounds of the invention wherein X is 2-haloethylamino are prepared by reaction of compounds of the invention wherein X is chlorine or bromine with ethyleneimine followed by treatment with isopropanolic hydrogen halide to give the desired comound.

The compounds of this invention are converted directly to useful products such as physiologically active compounds, or indirectly by conversion to other compounds of the invention more suitable as direct intermediates to useful physiologically active compounds. Thus, acids of Formula I can be reacted with 2-dialkylaminoalkyl halides (or salts thereof) such as 2-(diethylamino)ethyl bromide and its hydrochloride salt in the presence of an acid acceptor, such as potassium bicarbonate or sodium carbonate in an inert solvent such as toluene or benzene to give 2-dialkylaminoalkylene esters of fluoroalkoxy-substituted aromatic acids. Such compounds are also prepared by transesterification of esters of Formula I with a dialkylaminoalkanol such as 2-diethylaminoethanol.

The 2-dialkylaminoalkylene esters of fluoroalkoxy-substituted aromatic acids are active local anesthetics when tested by well-known screening methods, and in particular by the corneal reflex test on rabbits described in detail by Luduena and Hoppe, J. Pharm. Exptl. Therap., 104:40, 1952. Compounds active as local anesthetics prepared from the compounds of the present invention include:

2-(diethylamino)ethyl 2'-(2,2,2-trifluoroethoxy)-2'-naphthoate 2-(diethylamino)ethyl 2',5'-di-(2,2,2-trifluoroethoxy)-benzoate 2-(diethylamino)ethyl 1'-(2,2,2-trifluoroethoxy)-2'-naphthoate and pharmaceutically acceptable salts of these compounds.

The compounds of the invention can also be utilized to prepare physiologically active antiarrhythmic compounds by reaction of compounds of Formula I wherein X is halogen with a 2-(dialkylamino)alkylamine in an inert solvent, such as benzene, toluene or diethyl ether. Alternatively compounds of Formula I wherein X is —OR may be reacted with 2-(dialkylamino)alkylamines. Compounds of the invention wherein X is 2-haloethylamino are converted to active antiarrhythmics by reaction with appropriate secondary amines. The N-(2-dialkylaminoalkylene)amides of polyfluoroalkoxy-substituted aryl acids which are prepared from the compounds of the present invention are active antiarrhythmics according to a well-known screening method described in detail by Lawson in J. Pharm. Expt. Therap., 160:22, 1968. The activity is manifested in the ability to block chloroform-induced ventricular fibrillation in mice. Compounds particularly active as antiarrhythmics prepared from the compounds of the present invention include:

N-(2-diethylaminoethyl)-2-(2,2,2-trifluoroethoxy)-benzamide

N-(2-diethylaminoethyl)-3-(2,2,2-trifluoroethoxy)-benzamide

N-(2-diethylaminoethyl)-4-(2,2,2-trifluoroethoxy)-benzamide

N-(2-diethylaminoethyl)-2,4-di-(2,2,2-trifluoroethoxy)-benzamide

N-(2-diethylaminoethyl)-2,5-di-(2,2,2-trifluoroethoxy)-benzamide

N-(2-diethylaminoethyl)-2,6-di-(2,2,2-trifluoroethoxy)-benzamide

N-(2-diethylaminoethyl)-3,4-di-(2,2,2-trifluoroethoxy)-benzamide

N-(2-diethylaminoethyl)-1-(2,2,2-trifluoroethoxy)-2-naphthamide

N-(2-pyrrolidinylethyl)-3-(2,2,2-trifluoroethoxy)-2-naphthamide

N-(2-diethylaminoethyl)-2,4,6-tri-(2,2,2-trifluoroethoxy)benzamide and pharmaceutically acceptable salts of these compounds.

The following examples will more fully illustrate the preparation of the compositions of the invention. All temperatures in the examples are given in ° C.

EXAMPLE 1

Preparation of Methyl 2-(2,2,2-Trifluoroethoxy)benzoate

A mixture of methyl salicylate (6.4 ml., 7.6 g., 0.05 mole), 2,2,2-trifluoroethyl trifluoromethanesulfonate (13.9 g., 0.06 mole), anhydrous potassium carbonate (13.8 g., 0.1 mole) and acetone (150 ml.) is heated under reflux with efficient stirring for three days. The product is filtered and the filtrate is concentrated to a small volume. It is diluted with cold water and the resulting precipitate is collected and washed successively with cold dilute sodium hydroxide solution and water. The desired material is recrystallized then from aqueous ethanol to afford white solid, m.p. 61–62.

Analysis:

Calculated for $C_{10}H_9F_3O_3$: C, 51.3; H, 3.9; F, 24.3.
Found: C, 51.2; H, 4.1; F, 25.0.

EXAMPLE 2

Preparation of Methyl 1-(2,2,2-Trifluoroethoxy)-2-Naphthoate

A mixture containing 20.2 g. (0.1 mole) of methyl 1-hydroxy-2-naphthoate, 29 g. (0.125 mole) of 2,2,2-trifluoroethyl trifluoromethanesulfonate, 20 g. (0.2 mole) of anhydrous potassium bicarbonate and 200 ml. of dry acetone is refluxed for three days. Acetone is removed by distillation (steam bath). The residue is cooled and diluted with water. The resulting white solid is collected by filtration and washed successively with cold dilute sodium hydroxide solution and water. The solid is further purified by several recrystallizations from aqueous alcohol followed by sublimation, (oil bath, 60°–75°/0.2 mm. Hg.) to give white solid, m.p. 69.5°–70.5°.

Analysis:

Calculated for $C_{14}H_{11}F_3O_3$: C, 59.2; H, 3.9; F, 20.0.
Found: C, 58.9; H, 4.0; F, 21.1.

Additional compounds of the invention wherein X is OR are prepared according to the procedures described in Examples 1 and 2 and are listed in Table I.

TABLE I

| Example No. | Compound | Melting Point (in ° C.) |
| --- | --- | --- |
| 3 | methyl 3-(2,2,2-trifluoroethoxy)-benzoate | 57.5–59 |
| 4 | methyl 4-(2,2,2-trifluoroethoxy)-benzoate | 59.5–60.5 |
| 5 | ethyl 2,3-di-(2,2,2-trifluoroethoxy)benzoate | 30–31 |
| 6 | methyl 2,4-di-(2,2,2-trifluoroethoxy)benzoate | 70.5–71.5 |
| 7 | methyl 2,5-di-(2,2,2-trifluoroethoxy)benzoate | 42–44 |
| 8 | methyl 2,6-di-(2,2,2-trifluoroethoxy)benzoate | 52–54 |
| 9 | methyl 3,4-di-(2,2,2-trifluoroethoxy)benzoate | 57–59 |
| 10 | methyl 3,5-di-(2,2,2-trifluoroethoxy)benzoate | 81.5–82.5 |
| 11 | methyl 3,4,5-tri-(2,2,2-trifluoroethoxy)benzoate | 86–87 |
| 12 | methyl 3-(2,2,2-trifluoroethoxy)-2-naphthoate | 77–77.5 |

Compounds of the invention where *m* and *n* are greater than one are prepared according to the procedures described in Examples 1 and 2 utilizing intermediates of Formula III other than 2,2,2-trifluoroethyl trifluoromethanesulfonate are shown in Table II.

TABLE II

| Example No. | Starting Materials Formula II | Formula III | Product |
|---|---|---|---|
| 13 | methyl 2-hydroxybenzoate | 1,1-dihydroperfluoro-n-propyl trifluoromethanesulfonate | methyl 2-(1,1-dihydroperfluoro-n-propoxy)benzoate |
| 14 | methyl 2-hydroxybenzoate | 1,1,3-trihydroperfluoro-n-propyl trifluoromethanesulfonate | methyl 2-(1,1,3 trihydroperfluoro-n-propoxy)benzoate |
| 15 | ethyl 1-hydroxy-2-naphthoate | 1,1-dihydroperfluoro-n-butyl trifluoromethanesulfonate | ethyl 1-(1,1-dihydroperfluoro-n-butoxy)-2-naphthoate |
| 16 | methyl 2,4,6-trihydroxybenzoate | 1,1-dihydroperfluoro-n-propyl trifluoromethanesulfonate | methyl 2,4,6-tri-(1,1-dihydroperfluoro-n-propoxy)-benzoate |
| 17 | n-propyl 2,5-dihydroxybenzoate | 1,1-dihydroperfluoro-isobutyryl trifluoromethanesulfonate | n-propyl 2,5-di-(1,1-dihydroperfluoroisobutoxy)benzoate |
| 18 | methyl 4-hydroxybenzoate | 2,2-difluoro-2-(trifluoromethoxy)ethyl trifluoromethanesulfonate | methyl 4-[2,2-difluoro-2-(trifluoromethoxy)-ethoxy]benzoate |

An example of preparation of a compound of Formula I wherein X is $OCH_2C_mF_{2m}Y$ is given in Example 19.

EXAMPLE 19

Preparation of 2',2',2'-Trifluoroethyl 2,5-di-(2,2,2-trifluoroethoxy)benzoate

To a stirred refluxing suspension of 2,5-dihydroxybenzoic acid (88.3 g., 0.573 mole), potassium bicarbonate (573 g., 5.73 mole) and acetone (2.4 l.) is added dropwise 2,2,2-trifluoroethyl trifluoromethanesulfonate (564 g., 2.43 mole) in acetone (230 ml.). The mixture is maintained at reflux temperature for 48 hours, then additional 2,2,2-trifluoroethyl trifluoromethanesulfonate (139 g., 0.60 mole) in acetone is added and refluxing is continued for 24 hours. The acetone is removed by evaporation in vacuo, then the residue is added to water (2 l.). The aqueous layer is extracted with diethyl ether, and the ether layer is washed with saturated aqueous sodium chloride, then dried over sodium sulfate. The ether is evaporated in vacuo, then the residue is distilled to give 2',2',2'-trifluoroethyl 2,5-di-(2,2,2-trifluoroethoxy)benzoate, b.p. 91°–96° C./0.2 mm.

EXAMPLE 20

Using the method of Example 19, 2,4,6-trihydroxybenzoic acid is reacted with 2,2,2-trifluoroethyl trifluoromethanesulfonate to give 2',2',2'-trifluoroethyl 2,4,6-tri-(2,2,2-trifluoroethoxy)benzoate, m.p. 64.8° to 65.8°.

EXAMPLE 21

Preparation of 2-(2,2,2-Trifluoroethoxy)benzoic Acid

Methyl 2-(2,2,2-trifluoroethoxy)benzoate (8 g., 34.2 mmoles) potassium hydroxide (3.3 g., 350 mmoles), water (50 ml.) and alcohol (25 ml.) are heated together under reflux for 1.5 hours, and distilled until ca. 25 ml. of distillate is removed. The cooled residue is acidified (pH 3) and the resulting white solid is collected and recrystallized (aqueous alcohol) to give fluffy white solid, m.p. 85°–86.5° C.

Analysis:

Calculated for $C_9H_7F_3O_3$: C, 49.1; H, 3.2; F, 25.9. Found: C, 48.8; H, 3.3; F, 26.2.

EXAMPLE 22

Preparation of 1-(2,2,2-Trifluoroethoxy)-2-Naphthoic Acid

A mixture of 10 g. (35 mmoles) of methyl 1-(2,2,2-trifluoroethoxy)-2-naphthoate, 2.9 g., (42 mmoles) of potassium hydroxide, 50 ml. of ethanol and 40 ml. of water is refluxed for one hour, chilled and acidified. The fluffy precipitate is collected, water washed, and air-dried. It is purified by recrystallization first from chloroform and then from aqueous alcohol, m.p. 171.5°–172° C.

Analysis:

Calculated for $C_{13}H_9F_3O_3$: C, 57.8; H, 3.4; F, 21.1. Found: C, 57.8; H, 3.6; F, 21.7.

Compounds of the invention of Formula I wherein X is OH are obtained from each of the products of Examples 3 through 12 by the methods described in detail in Examples 21 and 22. Such products are listed in Table III.

TABLE III

| Example No. | Compound | Melting Point (in ° C.) |
|---|---|---|
| 23 | 3-(2,2,2-trifluoroethoxy)benzoic acid | 105–105.5 |
| 24 | 4-(2,2,2-trifluoroethoxy)benzoic acid | 200–200.5 |
| 25 | 2,3-di-(2,2,2-trifluoroethoxy)benzoic acid | 141–143 |

TABLE III-continued

| Example No. | Compound | Melting Point (in °C.) |
|---|---|---|
| 26 | 2,4-di-(2,2,2-trifluoroethoxy)benzoic acid | 143.5–144 |
| 27 | 2,5-di-(2,2,2-trifluoroethoxy)benzoic acid | 122–124 |
| 28 | 2,6-di-(2,2,2-trifluoroethoxy)benzoic acid | 158–159 |
| 29 | 3,4-di-(2,2,2-trifluoroethoxy)benzoic acid | 143–144 |
| 30 | 3,5-di-(2,2,2-trifluoroethoxy)benzoic acid | 141.5–143 |
| 31 | 2,4,6-tri-(2,2,2-trifluoroethoxy)-benzoic acid | 140.5–141.5 |
| 32 | 3,4,5-tri-(2,2,2-trifluoroethoxy)-benzoic acid | 196–197 |
| 33 | 3-(2,2,2-trifluoroethoxy)-2-naphthoic acid | 149–150 |

Compounds of the invention wherein X is OH and $m$ and $n$ are greater than one are prepared according to the procedures described in Examples 21 and 22 and listed in Table IV.

TABLE IV

| Example No. | Starting Material | Product |
|---|---|---|
| 34 | methyl 2-(1,1-dihydroperfluoro-n-propoxy)benzoate | 2-(1,1-dihydroperfluoro-n-propoxy)-benzoic acid |
| 35 | methyl 2-(1,1,3-trihydroperfluoro-n-propoxy)-benzoate | 2-(1,1,3-trihydroperfluoro-n-propoxy)benzoic acid |
| 36 | ethyl 1-(1,1-dihydroperfluoro-n-butoxy)-2-naphthoate | 1-(1,1-dihydroperfluoro-n-butoxy)-2-naphthoic acid |
| 37 | methyl 2,4,6-tri-(1,1-dihydroperfluoro-n-propoxy)benzoate | 2,4,6-tri-(1,1-dihydroperfluoro-n-propoxy)-benzoic acid |
| 38 | n-propyl 2,5-di-(1,1-dihydroperfluoroisobutoxy)-benzoate | 2,5-di-(1,1-dihydroperfluoroisobutoxy)benzoic acid |
| 39 | methyl 4-[2,2-difluoro-2-(trifluoromethoxy)ethoxy]-benzoic acid | 4-[2,2-difluoro-2-(trifluoromethoxy)ethoxy]-benzoic acid |

EXAMPLE 40

Preparation of N-(2-Chloroethyl)-2,4-di-(2,2,2-trifluoroethoxy)-benzamide

Ethyleneimine (2.9 g., 0.068 mole), triethylamine (6.8 g., 0.068 mole) and diethyl ether (250 ml.) are cooled to 0° C. and stirred while adding 2,5-di-(2,2,2-trifluoroethoxy)benzoyl chloride (22.8 g., 0.068 mole). The mixture is allowed to warm to room temperature and filtered. The filtrate is treated with 6.6 N isopropanol-hydrochloric acid mixture and filtered and the solvent evaporated in vacuo to give N-(2-chloroethyl)-2,5-di-(2,2,2-trifluoroethoxy-benzamide, m.p. 87°–88.5° C.

Analysis:
Calculated for $C_{13}H_{12}ClF_6NO_3$: C, 41.5; H, 3.2; N, 3.6. Found: C, 41.1; H, 3.2; N, 3.7.

EXAMPLE 41

Preparation of 1-(2,2,2-Trifluoroethoxy)-2-naphthoyl Chloride

A mixture of 10 g. (37 mmoles) of 1-(2,2,2-trifluoroethoxy)-2-naphthoic acid, 21.8 ml. (35.7 g., 300 mmoles) of purified thionyl chloride and 3 drops of dimethylformamide is refluxed for one hour. Excess thionyl chloride is removed in vacuo at water aspirator pressure while heating on a steam bath. Last traces of thionyl chloride are removed by vacuum distillation with added benzene. The product is 1-(2,2,2-trifluoroethoxy)-2-naphthoyl chloride according to infrared spectral measurement.

EXAMPLE 42

Preparation of 2,5-Di-(2,2,2-trifluoroethoxy)benzoyl Chloride

To 9.4 g. (30 mmoles) of 2,5-di-(2,2,2-trifluoroethoxy)benzoic acid are added 2 drops of dimethylformamide and 7.2 ml. (11.9 g., 100 mmoles) of purified thionyl chloride. The product is refluxed for 3 hours and excess thionyl chloride is removed in vacuo (steam bath/water aspirator pressure). Last traces of thionyl chloride are removed by similar vacuum distillation with added benzene. The product is 2,5-di-(2,2,2-trifluoroethoxy)benzoyl chloride according to infrared spectral measurement.

EXAMPLE 43

Preparation of 4-(2,2,2-Trifluoroethoxy)benzamide

A solution of methyl 4-(2,2,2-trifluoroethoxy)-benzoate (3 g., 0.013 mole) in methanol (25 ml.) is cooled using a dry-ice acetone bath, and the solution is saturated with anhydrous ammonia, then heated in a pressure reactor at 110° for 10 hours. The methanolic solution is filtered and the filtrate is evaporated. The residue is chromatographed on neutral alumina and the early fractions which elute rapidly with ethyl acetate are discarded, methyl ethyl ketone fractions are discarded and methanol fractions finally give a tan solid when evaporated. When recrystallized from ethanol the white solid is found to be 4-(2,2,2-trifluoroethoxy)-benzamide, m.p. 177°–178° C.

Analysis:
Calculated for $C_9H_8F_3NO_2$: C, 49.3; H, 3.7; F, 26.0; N, 6.4. Found: C, 49.5; H, 3.8; F, 26.0; N, 6.4.

EXAMPLE 44

Preparation of 4-(2,2,2-Trifluoroethoxy)benzamide

To 4-(2,2,2-trifluoroethoxy)benzoic acid (2.2 g., 0.01 mole) is added thionyl chloride (23.8 g., 0.2 mole) and the mixture is heated at reflux temperature for two hours. Excess thionyl chloride is removed by distillation on a steam bath at water aspirator pressure. Cold concentrated ammonium hydroxide is added in small portions to the cooled 4-(2,2,2-trifluoroethoxy)benzoyl chloride. The white solid product is collected by filtration and recrystallized from ethanol, m.p. 177°–178°. Its infrared spectrum is identical to that of the product of Example 43.

Compounds of the invention of Formula I wherein X is $NH_2$ are obtained by the methods described in detail in Examples 43 and 44. Such products are listed in Table V.

TABLE V

| Example No. | Product | Melting Point (in °C.) |
|---|---|---|
| 45 | 3-(2,2,2-trifluoroethoxy)benzamide | 146.5–147.5 |
| 46 | 3,4-di-(2,2,2-trifluoroethoxy)benzamide | 172–173 |
| 47 | 2,5-di-(2,2,2-trifluoroethoxy)benzamide | 131–133 |
| 48 | 3,4,5-tri-(2,2,2-trifluoroethoxy)-benzamide | 146–147 |
| 49 | 2-(2,2,2-trifluoroethoxy)benzamide | 143–144.5 |
| 50 | 2,4,6-tri-(2,2,2-trifluoroethoxy)-benzamide | 121–122 |
| 51 | 3,5-di-(2,2,2-trifluoroethoxy)benzamide | 127.5–128.5 |
| 52 | 2,6-di-(2,2,2-trifluoroethoxy)benzamide | 115–116 |
| 53 | 2,4-di-(2,2,2-trifluoroethoxy)benzamide | 135–136 |
| 54 | 3-(2,2,2-trifluoroethoxy)-2-naphthamide | 169–170 |
| 55 | 1-(2,2,2-trifluoroethoxy)-2-naphthamide | 182–183.5 |

Compounds of the invention wherein X is $NH_2$ and $m$ is greater than one are obtained by the methods described in Examples 43 and 44 and are listed in Table VI.

TABLE VI

| Example No. | Starting Material | Product |
|---|---|---|
| 56 | 2-(1,1-dihydroperfluoro-n-propoxy)benzoic acid | 2-(1,1-dihydroperfluoro-n-propoxy)benzamide |
| 57 | n-propyl 2,5-di-(1,1-di-hydroperfluoroisobutoxy)-benzoic acid | 2,5-di-(1,1-dihydroperfluoroisobutoxy)benzamide |
| 58 | 2,(1,1,3-trihydroperfluoro-n-propoxy)benzoic acid | 2-(1,1,3-trihydroperfluoro-n-propoxy)benzamide |
| 59 | 4-[2,2-difluoro-2-(trifluoromethoxy)ethoxy]-benzoic acid | 4-[2,2-difluoro-2-(trifluoromethoxy)ethoxy]benzamide |
| 60 | 1-(1,1-dihydroperfluoro-n-butoxy)-2-naphthoic acid | 1-(1,1-dihydroperfluoro-n-butoxy)-2-naphthamide |

EXAMPLE 61

Preparation of 2-(2,2,2-Trifluoroethoxy)benzoic Acid Hydrazide

Methyl 2-(2,2,2-trifluoroethoxy)benzoate (1.22 g. 5.2 mmole), ethanol (15 ml.) and 5 ml. of 95 per cent hydrazine (4.75 g., 158 mmole) are refluxed for two hours, cooled, diluted with water (100 ml.) and cooled. The white solid product, 2-(2,2,2-trifluoroethoxy)benzoic acid hydrazide is recrystallized from ethanol, m.p. 102°–104°.

Analysis:
Calculated for $C_9H_9F_3N_2O_2$: C, 46.2; F, 24.3; N, 12.0.
Found: C, 46.3; F, 25.3; N, 12.0.

EXAMPLE 62

Preparation of 2,6-Di-(2,2,2-trifluoroethoxy)benzoic Acid Hydrazide

Thionyl chloride (11.9 g., 100 mmole), 2,6-di(2,2,2-trifluoroethoxy)benzoic acid (2.0 g., 6.3 mmole) and two drops of dimethyl formamide are heated to reflux temperature and maintained at reflux for 4 hours. Unreacted thionyl chloride is removed by distillation on a steam bath at water aspirator pressure. The residue is dissolved in dry tetrahydrofuran and added dropwise to a solution of 95 per cent hydrazine (3.2 g., 100 mmole) in ethanol (15 ml.). The mixture is allowed to sit overnight and evaporate to dryness. The residue is diluted with water and a white solid collected and purified by sublimation (138°–140°/0.2 to 0.5 mm. Hg.) followed by recrystallization from benzene to give 2,6-di-(2,2,2-trifluoroethoxy)benzoic acid hydrazide, m.p. 153°–154° C.

Analysis:
Calculated for $C_{11}H_{10}F_6N_2O_3$: C, 39.8; H, 3.0; F, 34.4; N, 8.4. Found: C, 39.8; H, 2.9; F, 34.2; N, 8.3.

Compounds of the invention of Formula I wherein X is hydrazino are obtained by the methods described in detail in Examples 61 and 62 are are listed in Table VII.

TABLE VII

| Example No. | Compound | Melting Point (In °C.) |
|---|---|---|
| 63 | 3,4-di-(2,2,2-trifluoroethoxy)benzoic acid hydrazide | 129–130.5 |
| 64 | 2,5-di-(2,2,2-trifluoroethoxy)benzoic acid hydrazide | 89–92.5 |
| 65 | 3,4,5-tri-(2,2,2-trifluoroethoxy)-benzoic acid hydrazide | 130.5–131 |
| 66 | 3,5-di-(2,2,2-trifluoroethoxy)benzoic acid hydrazide | 121–122.5 |
| 67 | 2,4-di-(2,2,2-trifluoroethoxy)benzoic acid hydrazide | 111.5–112 |
| 68 | 3-(2,2,2-trifluoroethoxy)benzoic acid hydrazide | 123.5–124 |
| 69 | 2,4,6-tri-(2,2,2-trifluoroethoxy)-benzoic acid hydrazide | 136–137 |
| 70 | 1-(2,2,2-trifluoroethoxy)-2-naphthoic acid hydrazide | 117–119 |
| 71 | 3-(2,2,2-trifluoroethoxy)-2-naphthoic acid hydrazide | 153–155 |

Compounds of the invention wherein X is hydrazino and m is greater than one are prepared by the methods described in Examples 61 and 62 and are listed in TABLE VIII.

TABLE VIII

| Example No. | Starting Material | Product |
|---|---|---|
| 72 | 2-(1,1-dihydroperfluoro-n-propoxy)benzoic acid | 2-(1,1-dihydroperfluoro-n-propoxy)benzoic acid hydrazide |
| 73 | n-propyl 2,5-di-(1,1-dihydroperfluoroisobutoxy)-benzoid acid | 2,5-di-(1,1-dihydroperfluoroisobutoxy)benzoic acid hydrazide |
| 74 | 2-(1,1,3-trihydroperfluoro-n-propoxy)benzoic acid | 2-(1,1,3-trihydroperfluoro-n-propoxy)benzoic acid hydrazide |
| 75 | 4-[2,2-difluoro-2-(trifluoromethoxy)ethoxy]-benzoic acid | 4-[2,2-difluoro-2-(trifluoromethoxy)ethoxy]-benzoic acid hydrazide |
| 76 | 1-(1,1-dihydroperfluoro-n-butoxy)-2-naphthoic acid | 1-(1,1-dihydroperfluoro-n-butoxy)-2-naphthoic acid hydrazide |

EXAMPLE 77

Preparation of Sodium 2-(2,2,2-Trifluoroethoxy)benzoate 2-(2,2,2-Trifluoroethoxy)benzoic acid is dissolved in ethanol and treated with an equimolar amount of sodium hydroxide dissolved in a minimum amount of ethanol and stirred for one hour. The solvent is removed by evaporation in vacuo to give sodium 2-(2,2,2-trifluoroethoxy)benzoate.

Other salts of the invention are readily prepared in an analogous manner.

What is claimed is:

1. A compound of the formula

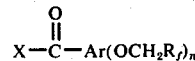

wherein X is amino, 2-chloroethylamine, 2-bromoethylamino or hydrazino, Ar is a benzene nucleus, each $R_f$ is a fluorocarbon group consisting of a fluorinated alkyl group having no more than one hydrogen on any carbon atom therein and containing from 1 to 3 carbon atoms, provided that two carbon atoms in the $R_f$ group can be linked together by an oxygen atom, and $n$ is 2.

2. A compound according to claim 1 wherein $R_f$ is $CF_3$.

3. 2,5-di-(2,2,2-trifluoroethoxy)-benzamide according to claim 1.

4. 2,5-di-(2,2,2-trifluoroethoxy)benzoic acid hydrazide according to claim 1.

5. A compound of the formula

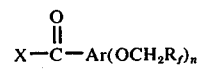

wherein X is amino, 2-chloroethylamino, 2-bromoethylamino or hydrazino, Ar is a naphthalene nucleus, each $R_f$ is a fluorocarbon group consisting of a fluorinated alkyl group having no more than one hydrogen on any carbon atom therein and containing from 1 to 3 carbon atoms, provided that 2 carbon atoms in the $R_f$ group can be linked together by an oxygen atom, and $n$ is 1–3.

6. A compound according to claim 5 wherein $R_f$ is $CF_3$.

7. A compound according to claim 5 wherein $n$ is 1.

8. 1-(2,2,2-trifluoroethoxy)-2-naphthamide according to claim 5.

9. 1-(2,2,2-trifluoroethoxy)-2-naphthoic acid hydrazide according to claim 7.

* * * * *